United States Patent
Lee et al.

(10) Patent No.: US 10,053,669 B2
(45) Date of Patent: *Aug. 21, 2018

(54) METHOD FOR DIFFERENTIATING PLURIPOTENT STEM CELL INDUCED FROM MESENCHYMAL STEM CELL INTO OSTEOBLAST

(71) Applicant: BBHC CO., LTD., Yongsan-gu, Seoul (KR)

(72) Inventors: Sang Yeon Lee, Uiwang-si (KR); Won Ju Jung, Seoul (KR); Ho Bin Kim, Seoul (KR); Min Sun Oh, Seoul (KR); Kye Ho Lee, Seoul (KR)

(73) Assignee: BBHC Co., Ltd., Seoul (KR)

(*) Notice: Subject to any disclaimer, the term of this patent is extended or adjusted under 35 U.S.C. 154(b) by 80 days.

This patent is subject to a terminal disclaimer.

(21) Appl. No.: 15/033,393

(22) PCT Filed: Nov. 5, 2013

(86) PCT No.: PCT/KR2013/009949
§ 371 (c)(1),
(2) Date: Apr. 29, 2016

(87) PCT Pub. No.: WO2015/064803
PCT Pub. Date: May 7, 2015

(65) Prior Publication Data
US 2016/0257935 A1    Sep. 8, 2016

(30) Foreign Application Priority Data

Nov. 1, 2013  (KR) .................. 10-2013-0132057

(51) Int. Cl.
*C12N 5/077* (2010.01)
*C12N 5/074* (2010.01)
*A61K 35/32* (2015.01)

(52) U.S. Cl.
CPC ............ *C12N 5/0654* (2013.01); *A61K 35/32* (2013.01); *C12N 5/0696* (2013.01); *C12N 2500/38* (2013.01); *C12N 2500/42* (2013.01); *C12N 2500/76* (2013.01); *C12N 2501/155* (2013.01); *C12N 2501/999* (2013.01); *C12N 2506/1369* (2013.01); *C12N 2506/45* (2013.01)

(58) Field of Classification Search
CPC ............... C12N 5/0654; C12N 5/0696; C12N 2500/38; C12N 2500/42; C12N 2501/155; C12N 2501/999; C12N 2506/1369; C12N 2506/45; C12N 2500/76; A61K 35/32

See application file for complete search history.

(56) References Cited

U.S. PATENT DOCUMENTS

2010/0135970 A1   6/2010  Kishore et al.

FOREIGN PATENT DOCUMENTS

| WO | 2006/123699 A1 | 11/2006 |
| WO | 2011/066403 A1 | 6/2011 |
| WO | 2011/016261 A1 | 10/2011 |

OTHER PUBLICATIONS

Elahi et al. Human Mesenchymal Stromal Cells from Different Sources Diverge in Their Expression of Cell Surface Proteins and Display Distinct Differentiation Patterns. Stem Cells International. vol. 2016, p. 1-9 (Year: 2016).*
Ribeiro et al. Mesenchymal stem cells from umbilical cord matrix, adipose tissue and bone marrow exhibit different capability to suppress peripheral blood B, natural killer and T cells. Stem Cell Research & Therapy 2013, 4:125, p. 1-16 (Year: 2013).*
Sacchetti et al. No Identical "Mesenchymal Stem Cells" at Different Times and Sites: Human Committed Progenitors of Distinct Origin and Differentiation Potential Are Incorporated as Adventitial Cells in Microvessels. Stem Cell Reports vol. 6, p. 897-913 (Year: 2016).*
Ahn et al. Enzymatic Extract from Ecklonia cava Induces the Activation of Lymphocytes by IL-2 Production Through the Classical NF-κB Pathway. Mar Biotechnol (2011) 13:66-73 (Year: 2011).*
Yokogawa et al. Inhibitory Effects of Ecklonia cava Extract on High Glucose-Induced Hepatic Stellate Cell Activation. Mar. Drugs 2011, 9, 2793-2808 (Year: 2011).*
Bilousova et al. Osteoblasts Derived from Induced Pluripotent Stem Cells Form Calcified Structures in Scaffolds Both in Vitro and in Vivo. Stem Cells 2011; 29:206-216 (Year: 2011).*
Jung et al. Concise Review: Induced Pluripotent Stem Cell-Derived Mesenchymal Stem Cells: Progress Toward Safe Clinical Products. Stem Cells. Jan. 2012 ; 30(1): 42-47. (Year: 2012).*
Ali, et al, "Phlorotannin-incorporated mesenchymal stem cells and their promising role in osteogenesis imperfecta," Journal of Medical Hypotheses and Ideas (2012) 6:85-89.
Wijesinghe, et al., "Biological activities and potential cosmeceutical applications of bioactive components from brown seaweeds: a review," Phytochem Rev, 2011, 10:431-443.
Okita, et al., "Induction of pluripotency by defined factors," Experimental Cell Research (2010) 316:2565-2570.
Lee, et al., "Molecular characteristics and anti-inflammatory activity of the fucodian extracted from Ecklonia cava," Carbohydrate Polymers, (2012) 89: 599-606.

(Continued)

*Primary Examiner* — Taeyoon Kim
(74) *Attorney, Agent, or Firm* — McDonnell Boehnen Hulbert & Berghoff LLP

(57) ABSTRACT

The present invention relates to a medium composition containing an *Ecklonia cava* extract for dedifferentiation an induced pluripotent stem cell. Also, the present invention relates to a method for differentiating an induced pluripotent stem cell produced by using the medium composition into osteoblasts. When using the medium composition according to the present invention, induced pluripotent stem cells using mesenchymal stem cells can be produced efficiently, and the pluripotent stem cells which have been produced can be useful as a cell treatment agent by being capable of being differentiated into osteoblasts.

5 Claims, 3 Drawing Sheets

(56) References Cited

OTHER PUBLICATIONS

Tashiro, et al. "Efficient Adipocyte and Osteoblast Differentiation from mouse induced pluripotent stem cells by adenoviral trasnduction," Stem Cells (2009) 27: 1802-1811.
Gang, et al., "In vitro mesengenic potential of human umbilical cord blood-derived mesenchymal stem cells," Biochemical and Biophysical Research Communications, 2004, 321:102-108.
Liu, et al. "n-Butylidenephthalide (BP) Maintains Stem Cell Pluripotency by Activating Jak2/Stat3 Pathway and Increases the Efficiency of iPS Cells Generation," PLOS One (2012) 7(9): e44024.
Kang, et al. "Effect of Dieckol, a Component of Scklonia cava, on the promotion of hair growth," Int J Mol Sci (2012), 13: 6407-6423.
Liu, et al., "Dedifferentiation-Reprogrammed Mesenchymal Stem Cells with Improved Therapeutic Potential," Stem Cells 2011;29:2077-2089.
Obokata, et al. "Stimulus-triggered fate conversion of somatic cells into pluripotency," Nature (2014) 505: 641 & Retraction in Nature (2014) 511:112.
Outani, et al. "Direct Induction of Chondrogenic cells from human dermal fibroblast culture by defined factors," PLOS One (2013) 8(10): e77365.

* cited by examiner

[Figure 1]
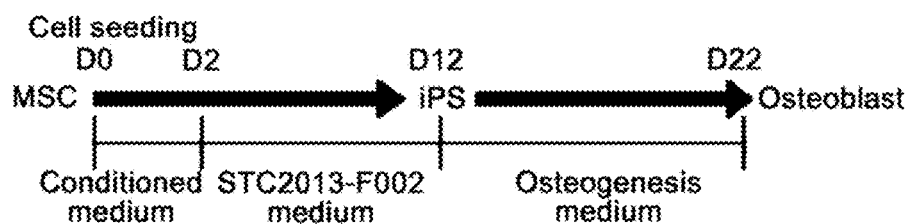
[Figure 2]
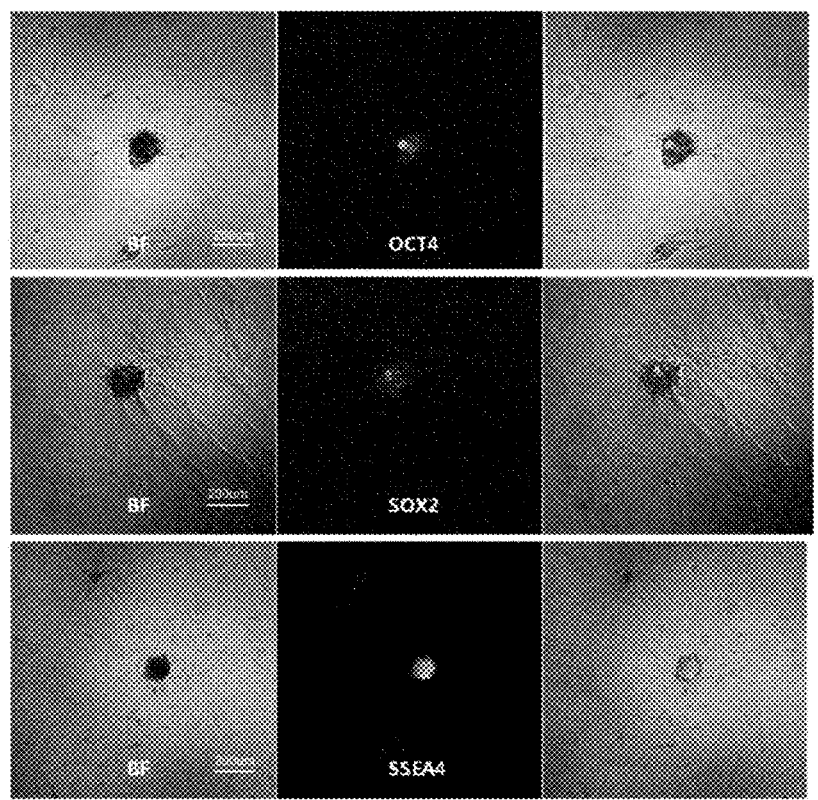

[Figure 3]
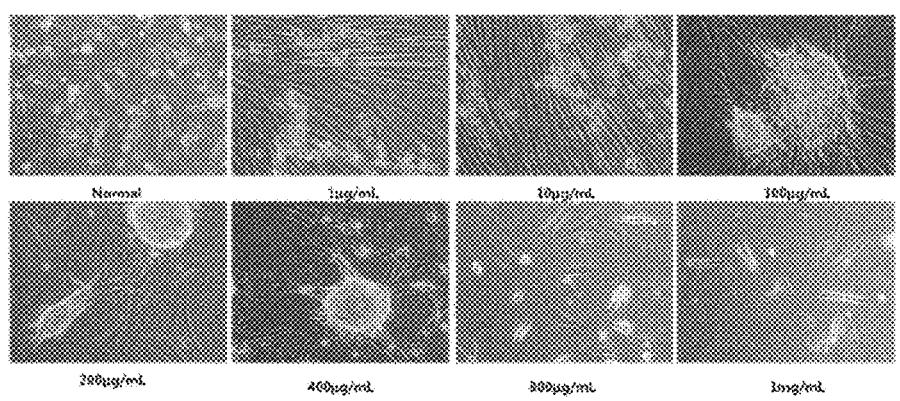
[Figure 4]
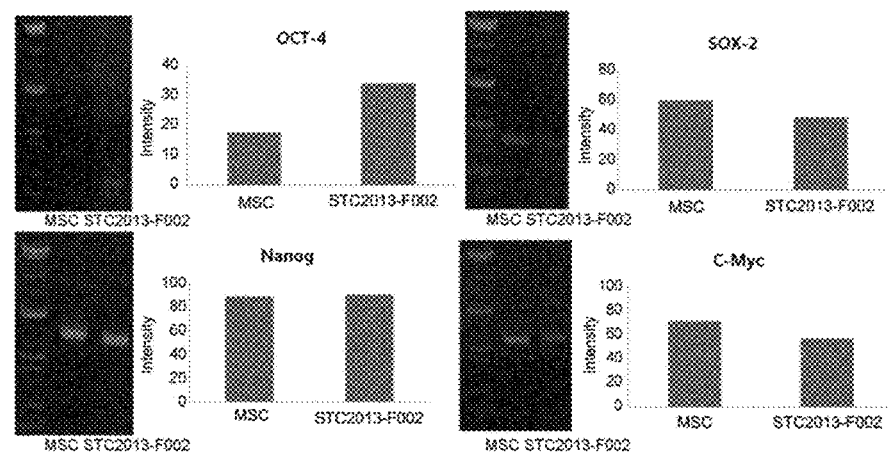

[Figure 5]
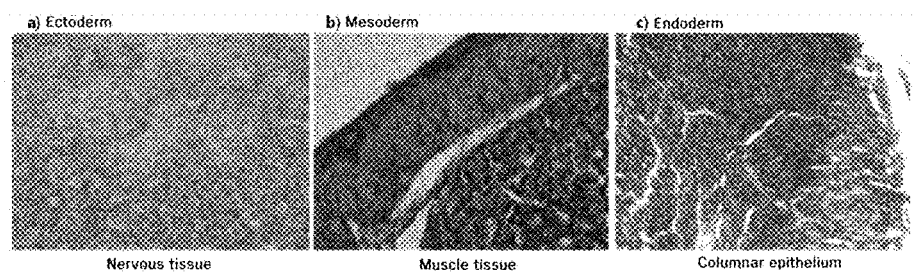
[Figure 6]
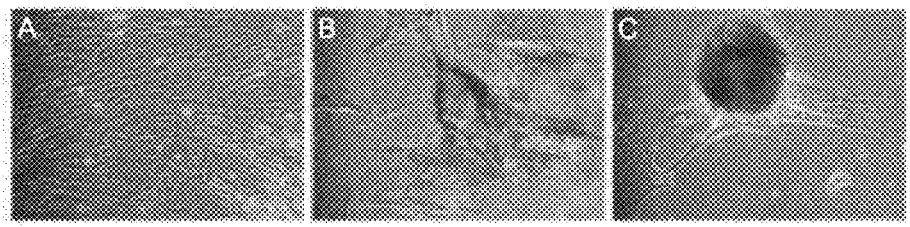

METHOD FOR DIFFERENTIATING PLURIPOTENT STEM CELL INDUCED FROM MESENCHYMAL STEM CELL INTO OSTEOBLAST

TECHNICAL FIELD

The present invention relates to a method comprising: producing induced pluripotent stem cells using a medium composition for inducing pluripotent stem cells from mesenchymal stem cells; and differentiating the induced pluripotent stem cells into osteoblasts.

BACKGROUND ART

Stem cells generally refer to undifferentiated cells before differentiation, which can be obtained from various tissues. Stem cells have properties capable of continuously producing cells identical to themselves for a certain amount of time in an undifferentiated state, and also have properties capable of differentiating into various types of cells, which constitute biological tissues, under proper conditions.

Stem cells can be broadly classified into embryonic stem cells and adult stem cells, according to their differentiation potential and creation time. In addition, stem cells can be classified according to their differentiation potential into pluripotent, multipotent, and unipotent stem cells.

Adult stem cells can be classified as multipotent or unipotent stem cells. Representative adult stem cells include mesenchymal stem cells (MSCs) and hematopoietic stem cells (HSCs). It is known that mesenchymal stem cells differentiate into chondrocytes, osteoblasts, adipocytes, myocytes, and neurons, and that hematopoietic stem cells mainly differentiate into blood cells in blood, such as erythrocytes, leukocytes, or platelets.

Meanwhile, pluripotent stem cells refer to stem cells having multipotency to differentiate into all three germ layers constituting the body, and thus are capable of differentiating into every cell or organ tissue of the human body. Generally, embryonic stem cells fall into this category. Human embryonic stem cells mise many ethical concerns, because they are created from embryos that may develop into human beings. However, embryonic stem cells are known as having an excellent ability to proliferate and differentiate, compared to adult stem cells. Adult stem cells cause less ethical issues, because they can be obtained from bone marrow, blood, brain, skin, and the like. However, adult stem cells have a limited ability to differentiate, compared to embryonic stem cells.

As a solution to overcome these problems, various techniques have been attempted to dedifferentiate cells derived from adult stem cells to thereby produce customized pluripotent stem cells similar to embryonic stem cells. Representative techniques include fusion with ES cells, somatic cell nuclear transfer, reprogramming by gene factor, and the like. According to fusion with ES cell, induced cells further have two pairs of genes, and this causes a problem in terms of stability of cells. Somatic cell nuclear transfer has problems in that it requires a large number of eggs and has very low efficiency. Reprogramming by gene factor is a technique of using viruses containing oncogenes to insert specific genes to thereby induce dedifferentiation, and this technique poses a high risk of cancer occurrence and is disadvantageous in terms of possibility of development of cell therapy products due to low efficiency and difficulty in terms of methods.

In order to obtain pluripotent stem cells successfully and abundantly, medium compositions in the stage of culturing isolated umbilical cord mononuclear cells are very important. Thus, studies are required to produce an increased amount of pluripotent stem cells by a highly efficient induction method.

The matters provided in the above background art are only intended to help better understand the background of the present invention. It should not be understood, however, that these matters fall within the prior art already known to a person having ordinary knowledge in the art.

DISCLOSURE

Technical Problem

The present inventors have made efforts to find a method for highly efficiently inducing pluripotent stem cells which provide cell therapy products with high safety and production efficiency in practice. As a result, the present inventors have found that when an *Ecklonia cava* extract, which is a safe natural extract, is added to a cell culture medium, induced pluripotent stem cells can be produced from mesenchymal stem cells using the medium composition, and the produced induced pluripotent stem cells can further be differentiated into osteoblasts in a safe and high efficient manner, thereby completing the present invention.

Therefore, it is an object of the present invention to provide a medium composition for dedifferentiating mesenchymal stem cells into induced pluripotent stem cells, which contains an *Ecklonia cava* extract.

Another object of the present invention is to provide a method comprising: dedifferentiating mesenchymal stem cells into induced pluripotent stem cells in a medium containing an *Ecklonia cava* extract; and differentiating the induced pluripotent stem cells into osteoblasts.

Yet another object of the present invention is to provide osteoblasts produced by the method.

Still another object of the present invention is to provide a cell therapy composition comprising the osteoblasts.

Other objects and advantages of the present invention will be more clearly understood by the following detailed description of the invention, the appended claims and the accompanying drawings.

Technical Solution

In accordance with one aspect of the present invention, there is provided a medium composition for dedifferentiating mesenchymal stem cells into induced pluripotent stem cells which are capable to differentiate into osteoblasts, the medium composition containing an *Ecklonia cava* extract.

In another aspect of the present invention, there is provided a method for differentiating mesenchymal stem cells into osteoblasts, comprising the steps of:

(a) adding an *Ecklonia cava* extract to a cell culture medium;

(b) dedifferentiating mesenchymal stem cells into induced pluripotent stem cells in the medium; and (c) differentiating the induced pluripotent stem cells into osteoblasts.

The present inventors have made efforts to find a method for inducing pluripotent stem cells which provide cell therapy products with high safety and production efficiency in practice without raising ethical concerns about the destruction of embryos. As a result, the present inventors have found that when an *Ecklonia cava* extract, which is a safe natural extract, is added to a cell culture medium, induced pluripotent stem cells can be produced with surprisingly high efficiency, and the induced pluripotent stem cells can further be differentiated into osteoblasts.

As used herein, the term "embryonic stem cells" refers to cells having pluripotency, which are isolated and cultured from the inner cell mass of a blastocyst, the first stage of development after fertilization. As used herein, the term "pluripotent stem cells" refers to stem cells having pluripotency, which are capable of differentiating into all three germ layers (i.e., endoderm, mesoderm and ectoderm) which constitute the body.

As used herein, the term "differentiation" refers to a process by which cells become more specialized in structure or function during cell growth through division and proliferation, i.e., a process by which cells, tissues, and the like of a living body change in shape or function in order to perform the given task.

As used herein, the term "cell therapy product," which is a pharmaceutical drug used for the purpose of treatment, diagnosis, and prevention with cells and tissues produced from human beings by isolation, culture, and specific manipulation, refers to a pharmaceutical drug which is used for the purpose of treatment, diagnosis, and prevention through a series of actions, such as changing biological properties of cells by proliferating or selecting allogeneic or xenogeneic cells in vitro, or by other ways, in order to restore functions of cells or tissues. The cell therapy products are broadly classified into a somatic cell therapy product and a stem cell therapy product, according to the degree of differentiation of cells. The present invention particularly relates to the stem cell therapy product.

The mesenchymal stem cells that are used in the present invention are cells isolated from embryonic stem cells or adult stem cells derived from mammals The mesenchymal stem cells are preferably umbilical cord mesenchymal stem cells, and more preferably human umbilical cord mesenchymal stem cells. The stem cells can be collected from the umbilical cord connecting the fetus and placenta in the human body. Collection of the mesenchymal stem cells from the umbilical cord can be performed using various methods. For example, a solution containing mononuclear cells can be obtained by collecting the umbilical cord from the human body, washing the collected umbilical cord with DPBS until blood no longer comes out, cutting the washed umbilical cord using a surgical blade, and incubating the cut umbilical cord at 37° C.

Hereinafter, each step of the method according to the present invention will be described in detail.

Step a) of Adding *Ecklonia cava* Extract to Cell Culture Medium

*Ecklonia cava*, an active ingredient contained in the medium composition of the present invention, is a perennial brown marine alga belonging to the order Laminariales, the family Lessoniaceae, which occurs mainly in the southern coast, and the ocean off Jeju-do and Ulleung-do, Korea. It is mainly fed by abalones, conches, and the like, and is used as main raw materials for preparing alginic acid, iodine, or potassium, or as foods.

The *Ecklonia cava* extract contained in the medium composition of the present invention may be prepared by extraction with water or an organic solvent, such as (a) an anhydrous or hydrous lower alcohol having 1 to 4 carbon atoms (methanol, ethanol, propanol, butanol, n-propanol, isopropanol and n-butanol, or the like), (b) a mixed solvent of the lower alcohol and water, (c) acetone, (d) ethyl acetate, (e) chloroform, (f) 1,3-butylene glycol, (g) hexane, (h) diethyl ether, or the like. Preferably it may be prepared by extraction with a mixed solvent of methanol or ethanol with water. When it is prepared by extraction with the mixed solvent, the content of methanol or ethanol in the mixed solvent is preferably 50 to 80 v/v %.

Recently, examples of applying the *Ecklonia cava* extract to skin compositions such as cosmetics have been increased (see Korean Patent Application Laid-open Nos. 2013-0017159, 2012-0040488 and 2010-0097293, etc.). However, an example of applying the *Ecklonia cava* extract to a medium for inducing pluripotent stem cells has not yet been reported.

As used herein, the term "medium" refers to a mixture for in vitro culture or differentiation of cells such as stem cells, which contains components essential for growth and proliferation of the cells, such as sugar, amino acids, various nutrients, serum, growth factors, minerals, and the like.

Various media are sold on the market in the art, and a medium may be artificially prepared and used. Media on the market include Dulbecco's Modified Eagle's Medium (DMEM), Minimal Essential Medium (MEM), Basal Medium Eagle (BME), RPMI 1640, F-10, F-12, DMEM F-12, α-Minimal Essential Medium (α-MEM), Glasgow's Minimal Essential Medium (G-MEM), Iscove's Modified Dulbecco's Medium (IMPM), AmnioMax complete Medium, AminoMall complete Medium (Gibco, N.Y., USA), Chang's Medium, MesemCult-XF Medium (STEMCELL Technologies, Vancouver, Canada), and the like. These media, as well as media that may be artificially produced, may be used as a basal medium that is contained in the medium composition of the present invention.

A serum component (e.g., Fetal Bovine Serum (FBS)), an antibiotic (e.g., penicillin, streptomycin), and the like, which are typically added, may be added to the basal medium. The concentration of the serum component or antibiotic component in the basal medium may vary within the range that can achieve the effect of the present invention. Preferably, the basal medium may contain 10% FBS, 100 unit/mL penicillin, 50 μg/mL streptomycin, and the like.

In addition, the medium of the present invention may further contain a nutrient mixture. The nutrient mixture is a mixture comprising various amino acids, vitamins, mineral salts, and the like, which are generally used in cell culture. The nutrient mixture may be prepared by mixing the amino acids, vitamins, mineral salts, and the like, or a commercially prepared nutrient mixture may be used. Examples of commercially prepared nutrient mixtures include, but are not limited to, M199, MCDB110, MCDB202, MCDB302, and the like.

In addition, the medium of the present invention may further contain energy water for the induction and stabilization of pluripotent stem cells. The energy water may be contained preferably in an amount of 0.01 to 10 v/v %, more preferably 0.05 to 0.5 v/v %.

The medium composition of the present invention is a medium specific for the induction of pluripotent stem cells, and can be prepared by adding the *Ecklonia cava* extract to the basal medium. The medium composition may preferably contain the *Ecklonia cava* extract at a concentration of 1 to 1,000 μg/mL, more preferably 100 to 400 μg/mL, based on the total medium composition.

Step b) of Dedifferentiating Mesenchymal Stem Cells into Induced Pluripotent Stem Cells Next, the mesenchymal stem cells are differentiated into induced pluripotent stem cells using the above-described medium.

In an example of the present invention, it could be seen that when the medium composition containing the *Ecklonia cava* extract according to the present invention was used, pluripotent stem cell colonies were formed on days 8 to 10 (FIGS. 2 and 3), unlike when DMEM F-12 medium alone was used.

The induced pluripotent stem cells produced in the present invention have the same differentiation potential as embryonic stem cells, and also have substantially the same shape as embryonic stem cells. In an example of the present invention, whether the genes (Nanog, Oct4, Sox-2, and Klf) and protein (SSEA4) characteristic of embryonic stem cells would be expressed was examined, and, as a result, it was shown that the genes and protein were expressed in the induced pluripotent stem cells of the present invention in the same manner as in embryonic stem cells (FIG. 4).

Step c) of Differentiating Induced Pluripotent Stem Cells into Osteoblasts

Next, the induced pluripotent stem cells produced as described above are differentiated into osteoblasts.

Differentiation of the induced pluripotent stem cells into osteoblasts may be performed using various differentiation media known in the art. Preferably, the differentiation is performed using a differentiation medium containing dexamethason, β-glycerol phosphate, ascorbic acid and bone morphogenic protein (BMP). Preferably, the differentiation medium contains 1-100 uM of dexamethason, 1-100 mM of β-glycerol phosphate, 0.01-50 mM of ascorbic acid, and 0.1-50 uM of BMP. The differentiation medium may also contain 3-isobutyl-1-methylxanthin, hydrocortisone and indomethacin.

As a basal medium for the differentiation medium, DMEM (Dulbecco's Modified Eagle's Medium), MEM (Minimal Essential Medium), BME (Basal Medium Eagle), RPMI 1640, F-10, F-12, DMEM F-12, α-MEM (α-Minimal Essential Medium), G-MEM (Glasgow's Minimal Essential Medium), IMPM (Iscove's Modified Dulbecco's Medium), AmnioMax complete Medium, AminoMax II complete Medium (Gibco, N.Y., USA), Chang's Medium, MesemCult-XF Medium (STEMCELL Technologies, Vancouver, Canada) or the like may be used.

The induced pluripotent stem cells produced in the present invention have the same pluripotency as embryonic stem cells. In an example of the present invention, it could be seen that the induced pluripotent stem cells produced in the present invention have pluripotency to differentiate into ectoderm, mesoderm and endoderm (FIG. 5).

Thus, the induced pluripotent stem cells produced in the present invention can effectively differentiate into osteoblasts.

In an example of the present invention, it could be seen that cells considered pluripotent stem cells could be differentiated into osteoblasts (FIG. 6).

In accordance with another aspect of the present invention, there is provided a cell therapy composition comprising the differentiated osteoblasts.

The cell therapy composition of the present invention may be administered by any route, particularly, an intraperitoneal or intrathoracic route, a subcutaneous route, an intravenous or intraarterial route, an intramuscular route, a topical route by injection, or the like.

In the present invention, the cell therapy composition may be administered in the form of injectable solution, suspension, emulsion, and the like, according to a conventional method. If necessary, the composition may be suspended in an adjuvant such as complete Freund's adjuvant, or may also be administered together with a substance having adjuvant activity, such as BCG. The composition may be sterilized, or may contain an adjuvant, such as a stabilizer, a hydrating agent, an emulsification accelerator, or a salt or buffer for controlling osmotic pressure, and other therapeutically useful substances. The composition may be prepared using a conventional mixing, granulation or coating method. The cell therapy composition according to the present invention may contain a pharmaceutically acceptable carrier or additive. Specifically, it may contain, in addition to the active ingredient, a diluent (e.g., dextrose, sorbitol, cellulose, glycine, lactose, sucrose, mannitol), a binder (e.g., magnesium aluminum silicate, starch paste, tragacanth, sodium carboxymethylcellulose), a disintegrant (e.g., starch, agar, alginic acid or its sodium salt), a boiling mixture and/or an absorbent, a sweetener, a flavor, and a colorant.

The cell therapy composition according to the present invention may be applied to various diseases, and can also be used as an allogeneic cell therapy product for humans based on the results of clinical tests on humans.

Advantageous Effects

The characteristics and advantages of the present invention are summarized as follows.

(i) The present invention provides a medium composition for dedifferentiating induced pluripotent stem cells, which contains an *Ecklonia cava* extract.

(ii) The present invention also provides a method for differentiating induced pluripotent stem cells, produced using the medium composition, into osteoblasts.

(iii) The use of the medium composition according to the present invention enables induced pluripotent stem cells to be efficiently produced from mesenchymal stem cells, and the produced pluripotent stem cell can differentiate into osteoblasts, and thus are useful as a cell therapy product.

DESCRIPTION OF DRAWINGS

FIG. 1 is a view illustrating that pluripotent stem cells that are substantially the same as embryonic stem cells are induced when mesenchymal stem cells are cultured using a medium containing an *Ecklonia cava* extract medium.

FIG. 2 shows the expression of specific proteins, which confirms that pluripotent stem cells induced by the method of the present invention are pluripotent stem cells.

FIG. 3 illustrates the formation of pluripotent stem cell colonies induced using various concentrations of an *Ecklonia cava* extract according to the method of the present invention.

FIG. 4 shows gene expression in pluripotent stem cells induced by the method of the present invention.

FIG. 5 shows the results of testing the in vivo differentiation potential of pluripotent stem cells induced by the method of the present invention.

FIG. 6 shows the results of differentiating pluripotent stem cells, induced by the method of the present invention, into osteoblasts by use of an osteoblast differentiation medium.

BEST MODE

Hereinafter, the present invention will be described in detail with reference to examples. These examples are only intended to describe the present invention in further detail, and it will be apparent to a person having ordinary knowledge in the art that the scope of the present invention is not limited to these examples.

EXAMPLES

Example 1

Preparation of *Ecklonia cava* Extract

An herbal sample used in the experiment was purchased from Jeju-do, and used in the experiment after precise accurate judgment. 100 g of a dried herbal sample was added to 1 L of 70% methanol, extracted under reflux for 16 hours, and filtered through a filter paper. The filtrate was concentrated in a rotary evaporator under reduced pressure, and then immediately, freeze-dried.

Example 2

Isolation and Culture of Mesenchymal Stem Cells from Human Umbilical Cord

Example 2-1

Collection of Human Umbilical Cord

Umbilical cord tissue was collected immediately after delivery. Before the tissue sample was transferred to the laboratory, it was rinsed clean, and then immediately, transferred into a 500 mL sterilized glass bottle containing F-12 medium and a transport medium (50 IU/mL of penicillin, 50 µg/mL of streptomycin (purchased from Invitrogen)). In the laboratory, extraction of stem cells was performed in a flow hood (Class 100) under sterile conditions. The sample was first transferred to a sterile stainless steel container. The umbilical cord tissue sample was washed several times with PBS, and then cut into 2 cm long pieces and transferred to a cell culture dish having a diameter of 10 cm. Herein, the sample was additionally washed and subjected to anti-infective treatment with 70% ethanol, and it was washed several times with PBS containing an antibiotic mixture (50 IU/mL of penicillin, 50 µg/mL of streptomycin (purchased from Invitrogen)) until the solution was clean.

Example 2-2

Isolation of Stem Cells from Human Umbilical Cord and Culture of Thereof

In order to isolate Wharton's jelly (base of umbilical cord) from the blood vessels and other internal elements of umbilical cord, the umbilical cord was first incised. After removing blood vessels, the isolated Wharton's jelly was cut into small pieces (0.5 cm×0.5 cm) in order to extract cells.

Explant was performed by placing the umbilical cord Wharton's jelly pieces in different tissue culture dishes having cell culture conditions suitable for extraction of epithelial stem cells or mesenchymal stem cells.

In order to isolate and culture mesenchymal stem cells, the explanted tissue was added to 5 mL of Dulbecco's modified eagle medium (DMEM) F-12 (Gibco) supplemented with 10% fetal bovine serum (FBS, Hyclone), 10% FBS, 100 unit/mL of penicillin and 50 µg/mL of streptomycin, and was maintained in a $CO_2$ incubator at 37° C. The medium was replaced every three or four days. The outgrowth of cells was monitored with an optical microscope. The outgrowing cells were treated with trypsin (0.125% trypsin/0.05% EDTA) for further expansion and frozen storage (using DMEM/10% FBS).

The medium was replaced every three or four days. The outgrowth of cells from the explanted tissue is monitored with an optical microscope.

In order to extract mesenchymal stem cells, the pellets of the cells were resuspended in medium DMEM F-12 (Gibco), 10% FBS, 100 unit/mL of penicillin, and 50 µg/mL of streptomycin and counted. Then, the cells were inoculated into 10-cm tissue culture dishes at a density of $1\times10^6$ cells/dish. The medium was replaced every three or four days. The growth of cells and formation of clones were monitored with an optical microscope. At a confluence of about 90%, the cells were sub-cultured as described above.

Experimental Example 1

Induction of Pluripotent Stem Cells from Mesenchymal Stem Cells

Experimental Example 1-1

Production of Pluripotent Stem Cells of Human Mesenchymal Stem Cells Using Various Concentrations of *Ecklonia cava* Extract An experiment for inducing pluripotent stem cells from human umbilical cord stem cells using various concentrations of the Jeju *Ecklonia cava* extract was performed. For a control group, the MSC culture medium DMEM F-12 (Gibco) (containing 10% FBS, 100 unit/mL of penicillin, and 50 µg/mL of streptomycin) was used as a basal medium. For an experimental group, 1 µg/mL, 10 µg/mL, 100 µg/mL, 200 µg/mL, 400 µg/mL, 800 µg/mL and 1000 µg/mL of the Jeju *Ecklonia cava* extract, and 0.1 v/v % of energy water (purified deionized water containing $SiO_2$, $Al_2O_3$, $TiO_3$, $Fe_2O_3$, CaO, $Na_2O$, $K_2O$, and LiO; STC Nara Co., Ltd., Korea), were added to media with human umbilical cord mesenchymal stem cells subcultured three times (FIG. 1). Human umbilical cord mesenchymal stem cells were isolated and washed, and the resulting mononuclear cells were inoculated into 6-well plates (dishes) at a density of $1\times10^4$ cells and cultured under the conditions of 37° C. and 5% $CO_2$.

For the pluripotent stem cells induced by the method of the present invention, the expressions of OCT4, SOX2 and stage-specific embryonic antigen4 (SSEA4), which are proteins specific for embryonic stem cells, were analyzed by immunochemical staining using antibodies against the proteins. For straining, the cells were fixed with 4% paraformaldehyde, washed with PBS, and blocked with 1% BSA solution. Then, the cells were treated with primary antibodies against OCT4, SOX3 and SSEA4 and incubated at 4° C. for 18 hours. Then, the cells were washed with PBS, and treated with fluorescence (FTTC)-labeled secondary antibodies against the primary antibodies and incubated at room temperature for 1 hour. After washing with PBS, expression of the proteins was analyzed using a confocal microscope, and the results of the analysis are shown in FIG. 2. In FIG. 2, BF indicates bright field, the second figure indicates the staining results for expression of each protein, and the third figure indicates the merge of the two figures (FIG. 2).

As a result, in the experimental group, it was observed that only when the concentration of the Jeju *Ecklonia cava* extract was between 100 and 400 µg/mL, colonies were formed after 10 days (FIG. 3). Further, OCT4, SOX2 and SSEA4, which are markers specific for pluripotent stem cells, were stained only in colonies, suggesting that the cells induced by the method of the present invention are pluripotent stem cells.

Experimental Example 1-2

Analysis and Comparison of Pluripotent Stem Cell Genes

Colonies were detached from the pluripotent stem cells (produced in Example 2-1 above) using a 200 µl pipette while observing the pluripotent stem cells with a microscope, and then total RNA was isolated using TRIzol reagent (manufactured by Invitrogen). cDNA was synthesized using reverse transcription-polymerase chain reaction (RT-PCR), and then PCR was performed using primers specific for OCT4, Sox-2, Nanog, c-Myc, and the control gene glyceraldehyde 3-phosphate dehydrogenase (GAPDH). Nanog, OCT4 and Sox-2 are characteristic genes appearing in embryonic stem cells, and c-Myc gene is a non-specific gene that may be positive in both embryonic stem cells and adult stem cells. The PCR products were analyzed by agarose gel electrophoresis to confirm the expression of these genes, and the results of the analysis are shown in FIG. 4. Referring to FIG. 4, the expression level of OCT4, which is a characteristic gene of pluripotent stem cells, was low in mesenchymal stem cells which did not undergo the induction process, whereas the expression levels of the characteristic genes were significantly high in the pluripotent stem cells (STC2013-F002) induced by the method of the present invention. SOX2 and Nanog, which are stem cell genes, were expressed at similar levels, and the expression level of c-Myc, a non-specific gene, was lower in cells (STC2013-F002) which underwent the induction process, than in the cells which did not undergo the induction process.

Experimental Example 2

Identification of Pluripotent Stem Cells by Teratoma Test

In order to analyze the in vivo differentiation potential of the pluripotent stem cells induced by the method of the present invention, undifferentiated pluripotent stem cell colonies cultured on support cells were detached by treatment with trypsin-EDTA at day 5 of culture, and then added to collagenase and maintained in an incubator for 30 minutes The undifferentiated pluripotent stem cells were recovered, and $1 \times 10^6$ cells were injected subcutaneously into mice with severe combined immune deficiency (SCID). After 4 weeks, formed teratomas were harvested, fixed with 4% paraformaldehyde, and embedded in paraffin according to a conventional method. The tissue was sectioned to a thickness of 10 µm and stained with hematoxylin and eosin.

Referring to FIG. 5, it can be seen that teratoma was visibly formed in the area into which the induced pluripotent stem cells produced by the method of the present invention were injected. Specifically, it was histologically shown that teratomas were formed which are capable of differentiating into ectoderm-derived nervous tissue (FIG. 5a), mesoderm-derived muscle tissue (FIG. 5b), and endoderm-derived stomach tissue (columnar epithelium, FIG. 5c). Through the experiment, it can be confirmed that the cells induced by the method of the present invention have substantially the same in vivo differentiation potential as embryonic stem cells, i.e., pluripotency to differentiate into ectoderm, mesoderm, and endoderm.

Experimental Example 3

Dedifferentiation into Osteoblasts

In order to induce differentiation into osteoblasts, mesenchymal stem cells were cultured in an incubator under the conditions of 95% humidity, 37° C. and 5% $CO_2$ by use of a medium comprising a mixture of the *Ecklonia cava* extract and energy water, thereby inducing pluripotent stem cells from the mesenchymal stem cells. Then, the cells were cultured in the osteoblast differentiation medium DMEM F-12 (containing 20 uM dexamethasone, 10 mM β-glycerol phosphate, 0.3 mM ascorbic acid, 1 uM BMP) for 2 weeks. In order to verify differentiation into osteoblasts, Von kossa histochemical staining was performed. As a result, as shown in FIG. 6, the cells were negative for Von kossa before treatment with the differentiation medium (FIG. 6A) and positive to Von kossa after treatment with the differentiation medium (FIGS. 6B and 6C), suggesting that the cells considered pluripotent stem cells could be differentiated into osteoblasts.

Although the present disclosure has been described in detail with reference to the specific features, it will be apparent to those skilled in the art that this description is only of a preferred embodiment thereof, and does not limit the scope of the present invention. Thus, the substantial scope of the present invention will be defined by the appended claims and equivalents thereof.

The invention claimed is:
1. A method for differentiating mesenchymal stem cells into osteoblasts, comprising the steps of:
   (a) adding 100-400 µg/ml of an *Ecklonia cava* extract to a cell culture medium, wherein the *Ecklonia cava* extract is extracted by water and/or organic solvent;
   (b) culturing mesenchymal stem cells in the medium to dedifferentiate the stem cells into induced pluripotent stem cells; and
   (c) culturing the induced pluripotent stem cells in an osteoblast differentiation medium to differentiate into osteoblasts.
2. The method of claim 1, wherein the *Ecklonia cava* extract is added to a basal medium selected from the group consisting of DMEM (Dulbecco's Modified Eagle's Medium), MEM (Minimal Essential Medium), BME (Basal Medium Eagle), RPMI 1640, F-10, F-12, DMEM-F12, α-MEM (α-Minimal Essential Medium), G-MEM (Glasgow's Minimal Essential Medium), IMDM (Iscove's Modified Dulbecco's Medium), and MacCoy's 5A medium.
3. The method of claim 1, wherein the cell culture medium further contains 0.01-10% v/v of purified deionized water containing $SiO_2$, $Al_2O_3$, $TiO_3$, $Fe_2O_3$, CaO, $Na_2O$, $K_2O$, and LiO.
4. The method of claim 1, wherein the osteoblast differentiation medium contains dexamethasone, β-glycerol phosphate, ascorbic acid and bone morphogenic protein (BMP).
5. The method of claim 4, wherein the osteoblast differentiation medium contains 3-isobutyl-1-methylxanthine, hydrocortisone and indomethacin and a basal medium selected from the group consisting of DMEM (Dulbecco's Modified Eagle's Medium), MEM (Minimal Essential Medium), BME (Basal Medium Eagle), RPMI 1640, F-10, F-12, DMEM-F12, α-MEM (α-Minimal Essential

Medium), G-MEM (Glasgow's Minimal Essential Medium), IMDM (Iscove's Modified Dulbecco's Medium), and MacCoy's 5A medium.

* * * * *